United States Patent [19]

Grantham

[11] 4,323,580
[45] * Apr. 6, 1982

[54] MITICIDAL, FUNGICIDAL AND OVICIDAL DIPHENYLSULFENAMIDES

[75] Inventor: Gary D. Grantham, Wilmington, Del.

[73] Assignee: E. I. Du Pont de Nemours and Company, Wilmington, Del.

[*] Notice: The portion of the term of this patent subsequent to Jul. 29, 1997, has been disclaimed.

[21] Appl. No.: 115,105

[22] Filed: Jan. 24, 1980

[51] Int. Cl.$^3$ .................... A01N 33/02; A01N 37/18; C07C 145/02
[52] U.S. Cl. .................................. 424/324; 424/330; 564/102
[58] Field of Search .................... 260/551 S; 424/330, 424/324; 564/102

[56] References Cited

FOREIGN PATENT DOCUMENTS

| 846205 | 3/1977 | Belgium . |
| 846419 | 3/1977 | Belgium . |
| 156 | 1/1979 | European Pat. Off. . |
| 4642 | 10/1979 | European Pat. Off. . |
| 1455207 | 11/1976 | United Kingdom . |

*Primary Examiner*—Allen J. Robinson

[57] ABSTRACT

Diphenyl sulfenamides, such as 1,1,1-trichloro-N-[2-chloro-5-(trifluoromethy)phenyl]-N-[2,6-ditrifluoromethyl-4-nitrophenyl]-methane-sulfenamide, useful for control of mites, plant diseases, and insect eggs.

12 Claims, No Drawings

MITICIDAL, FUNGICIDAL AND OVICIDAL DIPHENYLSULFENAMIDES

BACKGROUND OF THE INVENTION

This invention relates to miticidal, fungicidal and ovicidal sulfenamides.

British Pat. No. 1,455,207 discloses pesticidal diphenylamine derivatives of the formulas:

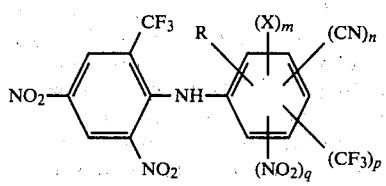

and

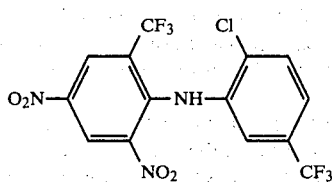

where X and R represent various substituents definitions.

Belgian Pat. No. 846,205 discloses compounds with utility as rodenticides of the formula

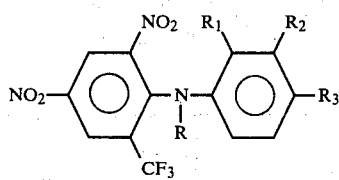

where R, $R_1$, $R_2$ and $R_3$ represent various defined substituents.

Belgian Pat. No. 846,419 discloses compounds with utility as delayed-action rodenticides of the formula

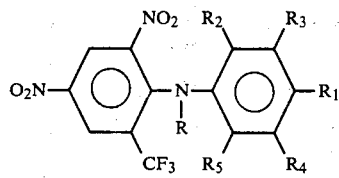

where R, $R_1$, $R_2$, $R_3$, $R_4$ and $R_5$ represent various defined substituents.

European Pat. No. 156 discloses benzotrifluoride derivatives with insecticidal, acaricidal, nematicidal, insect growth retardant, fungicidal and bactericidal activity. These compounds have the formula

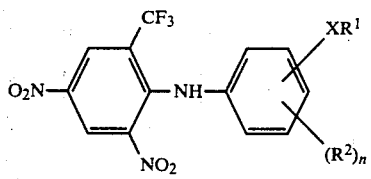

where $R^1$ and $R^2$ represent various defined substituents.

European Pat. No. 4642 discloses compounds useful as insecticides, acaricides, nematocides, fungicides and herbicides of the formula

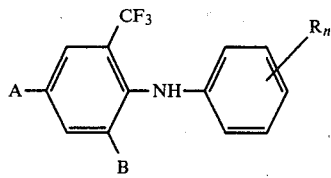

where A, B and R represent various defined substituents.

SUMMARY OF THE INVENTION

This invention relates to novel sulfenamides of Formula I, to methods for preparing them, and to compositions containing them, and to methods for using them to control mites, fungus disease of plants, and insect eggs.

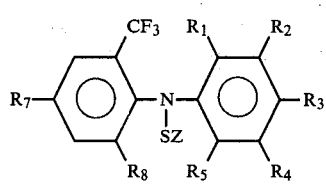

wherein $R_1$, $R_3$ and $R_4$ independently are H, F, Cl, Br, $NO_2$, $CF_3$, $OCF_3$, $OCF_2CF_2H$ or $S(O)_kR_6$;

$R_2$ is H, F, Cl, Br, $NO_2$ or $CF_3$;

$R_5$ is H or F;

k is 0, 1, or 2;

$R_6$ is $C_1$–$C_2$ alkyl or $C_1$–$C_2$ alkyl substituted with 2 to 4 atoms of Cl, F or combinations thereof;

$R_7$ is $NO_2$ or $CF_3$;

$R_8$ is $NO_2$ or $CF_3$;

Z is $CCl_3$, $CCl_2F$; $CCl_2CCl_2H$ or $CCl_2CFCl_2$;

provided that when $R_1$ is $NO_2$ or $CF_3$, then $R_3$ must be H or F;

provided that at least two of the substituents $R_1$, $R_2$, $R_3$, and $R_4$ are H, F or combinations thereof;

provided that when two of the substituents $R_1$, $R_2$, $R_3$ and $R_4$ are $NO_2$, $S(O)_kR_6$ or combinations thereof, they are not ortho to each other;

provided that $R_7$ and $R_8$ cannot both be $NO_2$ unless one of $R_1$, $R_3$, or $R_4$ is $S(O)_kR_6$; and provided that $R_7$ and $R_8$ cannot both be $CF_3$.

DETAILED DESCRIPTION OF THE INVENTION

Illustrative Compounds

Compounds which are illustrative of those which can be prepared are those compounds of Formula I where:

$R_2$ is H, F, Cl or Br;

$R_3$ is H, F, Cl, Br, or $S(O)_kR_6$;

$R_4$ is F, Cl, Br, $CF_3$, $OCF_3$, $OCF_2CF_2H$, or $S(O)_kR_6$.

Other compounds which can be prepared are compounds of Formula I where

Z is $CCl_3$;

$R_1$ and $R_4$ independently are Cl, $CF_3$, $OCF_3$, $OCF_2CF_2H$, or $S(O)_kR_6$;

$R_2$, $R_3$, and $R_5$ are H.

Synthesis

The compounds of the invention can be prepared by reacting compounds of Formula (II) with sulfenyl chlorides, ClSZ, in the presence of an acid acceptor in an inert solvent as outlined in the following scheme:

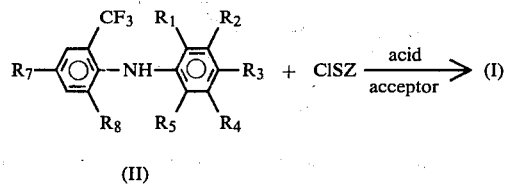

wherein $R_1$, $R_2$, $R_3$, $R_4$, $R_5$, $R_7$, $R_8$ and Z are as previously defined. Organic bases such as trimethylamine, triethylamine, or pyridine or inorganic bases such as sodium or potassium hydroxide, sodium or potassium carbonate, or sodium hydride may be used as the acid acceptor. Any inert solvent such as toluene, dioxane, tetrahydrofuran, ethyl ether, methylene chloride, etc., may be employed. The reaction is substantially complete at ambient temperature and pressure. Elevated temperature may be used if necessary to shorten reaction time.

The diphenylamines of Formula (II) can be obtained using the procedures described in British Pat. No. 1,455,207, European Pat. No. 156 or European Pat. No. 4642.

The compound, 1,1,1-trichloro-N-[2-chloro-5-(trifluoromethyl)phenyl]-N-[2,6-ditrifluoromethyl-4-nitrophenyl]-methanesulfenamide, can be made by the following procedure.

Slurry sodium hydride (1.2 equivalents) in anhydrous tetrahydrofuran under a nitrogen atmosphere at room temperature. Add dropwise with stirring a solution of 2-chloro-N-[2,6-ditrifluoromethyl-4-nitrophenyl]-5-(trifluoromethyl)-benzenamine (1 equivalent) in anhydrous tetrahydrofuran. After the addition is complete, stir the solution at ambient temperature for one hour. Add perchloromethyl mercaptan (1 equivalent) and stir for two hours. Pour the reaction mixture into water and extract with methylene chloride. Dry the organic extracts with $MgSO_4$ and concentrate in vacuo to give the crude product. Purify by a standard method to give 1,1,1-trichloro-N-[2-chloro-5-(trifluoromethyl)phenyl]-N-[2,6-ditrifluoromethyl-4-nitrophenyl]methylane sulfenamide.

By reacting equivalent amounts of other compounds of Formula II with ClSZ using the above procedure, the following compounds of Formula I can be prepared.

TABLE I

| $R_1$ | $R_2$ | $R_3$ | $R_4$ | $R_5$ | $R_7$ | $R_8$ |
|---|---|---|---|---|---|---|
| Cl | H | H | $SCH_3$ | H | $NO_2$ | $NO_2$ |
| Cl | H | H | $SOCH_3$ | H | $NO_2$ | $NO_2$ |
| $CF_3$ | H | H | $SO_2C_2H_5$ | H | $NO_2$ | $NO_2$ |
| $SCCl_2CH_3$ | H | H | $CF_3$ | H | $NO_2$ | $NO_2$ |
| $SCF_2CHF_2$ | H | H | $OCF_3$ | H | $NO_2$ | $NO_2$ |
| $OCF_2CHF_2$ | H | H | $SOCHCl_2$ | H | $NO_2$ | $NO_2$ |
| Cl | H | H | $SCH_2CF_3$ | H | $NO_2$ | $NO_2$ |
| Cl | H | $SCH_3$ | H | H | $NO_2$ | $NO_2$ |
| $OCF_3$ | H | $SO_2CCl_2CHCl_2$ | H | H | $NO_2$ | $NO_2$ |
| Br | H | $SCHCl_2$ | H | H | $NO_2$ | $NO_2$ |
| $SOCHF_2$ | H | $SOCF_3$ | H | H | $NO_2$ | $NO_2$ |
| $SO_2C_2H_5$ | H | $SO_2C_2H_5$ | H | H | $NO_2$ | $NO_2$ |
| Cl | H | H | $SCF_3$ | H | $NO_2$ | $NO_2$ |
| Br | H | H | $SCCl_3$ | H | $NO_2$ | $NO_2$ |
| $CF_3$ | H | H | $SO_2CF_2CHF_2$ | H | $NO_2$ | $NO_2$ |
| $OCF_2CF_2H$ | H | H | $SOCCl_2CHCl_2$ | H | $NO_2$ | $NO_2$ |
| Cl | H | H | $CF_3$ | H | $NO_2$ | $CF_3$ |
| Cl | H | H | $OCF_3$ | H | $NO_2$ | $CF_3$ |
| $OCF_2CHF_2$ | H | H | Cl | H | $NO_2$ | $CF_3$ |
| $OCF_3$ | H | H | $OCF_3$ | H | $NO_2$ | $CF_3$ |
| $SC_2H_5$ | H | H | $OCF_2CHF_2$ | H | $NO_2$ | $CF_3$ |
| Cl | H | H | $SO_2CCl_3$ | H | $NO_2$ | $CF_3$ |
| $CF_3$ | H | H | $SCHF_2$ | H | $NO_2$ | $CF_3$ |
| $SO_2CHCl_2$ | H | H | Cl | H | $NO_2$ | $CF_3$ |
| Cl | H | H | $SCCl_2CHCl_2$ | H | $NO_2$ | $CF_3$ |
| $SCH_3$ | H | H | $CF_3$ | H | $NO_2$ | $CF_3$ |
| F | H | H | $CF_3$ | H | $NO_2$ | $CF_3$ |
| Br | H | H | $OCF_3$ | H | $NO_2$ | $CF_3$ |
| Br | H | H | Br | H | $NO_2$ | $CF_3$ |
| H | Cl | H | $CF_3$ | H | $NO_2$ | $CF_3$ |
| H | Br | Br | H | H | $NO_2$ | $CF_3$ |
| H | F | H | F | H | $NO_2$ | $CF_3$ |
| H | H | Cl | H | H | $NO_2$ | $CF_3$ |
| H | H | F | H | H | $NO_2$ | $CF_3$ |
| H | H | F | H | H | $NO_2$ | $CF_3$ |
| H | H | H | H | F | $NO_2$ | $CF_3$ |
| $NO_2$ | H | H | H | H | $NO_2$ | $CF_3$ |
| H | H | $NO_2$ | H | H | $NO_2$ | $CF_3$ |
| Cl | H | H | $NO_2$ | H | $NO_2$ | $CF_3$ |

TABLE I-continued

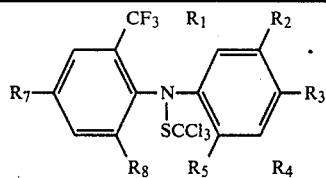

| R1 | R2 | R3 | R4 | R5 | R7 | R8 |
|---|---|---|---|---|---|---|
| Cl | H | H | SCCl$_2$F | H | NO$_2$ | CF$_3$ |
| OCF$_3$ | H | H | SO$_2$CH$_2$CCl$_3$ | H | NO$_2$ | CF$_3$ |
| Br | H | H | SCHFCCl$_3$ | H | NO$_2$ | CF$_3$ |
| Cl | H | H | OCF$_3$ | H | CF$_3$ | NO$_2$ |
| OCF$_3$ | H | H | Cl | H | CF$_3$ | NO$_2$ |
| SOCH$_3$ | H | H | SOCH$_3$ | H | CF$_3$ | NO$_2$ |
| Cl | H | CF$_3$ | H | H | CF$_3$ | NO$_2$ |
| CF$_3$ | H | H | H | H | CF$_3$ | NO$_2$ |
| H | H | CCF$_2$CF$_2$H | H | H | CF$_3$ | NO$_2$ |
| H | NO$_2$ | H | CF$_3$ | H | CF$_3$ | NO$_2$ |
| H | CF$_3$ | H | Cl | H | CF$_3$ | NO$_2$ |
| H | H | H | SO$_2$CHClCH$_2$F | H | CF$_3$ | NO$_2$ |

TABLE II

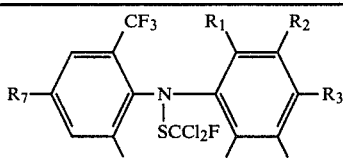

| R1 | R2 | R3 | R4 | R5 | R7 | R8 |
|---|---|---|---|---|---|---|
| Cl | H | H | SCH$_3$ | H | NO$_2$ | NO$_2$ |
| CF$_3$ | H | H | SOC$_2$H$_2$ | H | NO$_2$ | NO$_2$ |
| SO$_2$CCl$_2$H | H | H | OCF$_3$ | H | NO$_2$ | NO$_2$ |
| SO$_2$CH$_3$ | H | H | Br | H | NO$_2$ | NO$_2$ |
| Cl | H | H | CF$_3$ | H | NO$_2$ | CF$_3$ |
| OCF$_2$CF$_2$H | H | H | Cl | H | NO$_2$ | CF$_3$ |
| H | Br | H | CF$_3$ | H | NO$_2$ | CF$_3$ |
| Cl | H | SO$_2$CH$_3$ | H | H | NO$_2$ | CF$_3$ |
| Br | H | H | OCF$_2$CF$_2$H | H | CF$_3$ | NO$_2$ |
| OCF$_3$ | H | Cl | H | H | CF$_3$ | NO$_2$ |
| H | H | SCCl$_2$H | H | H | CF$_3$ | NO$_2$ |
| SCH$_3$ | H | H | H | H | CF$_3$ | NO$_2$ |
| SCF$_2$Cl | H | H | OCF$_3$ | H | NO$_2$ | NO$_2$ |
| H | H | SCHFCHI$_2$ | H | H | NO$_2$ | NO$_2$ |
| SO$_2$CHClCF$_3$ | H | H | Cl | H | NO$_2$ | NO$_2$ |

TABLE III

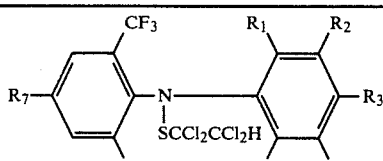

| R1 | R2 | R3 | R4 | R5 | R7 | R8 |
|---|---|---|---|---|---|---|
| Cl | H | H | SCF$_2$H | H | NO$_2$ | NO$_2$ |
| CF$_3$ | H | H | SCCl$_2$H | H | NO$_2$ | NO$_2$ |
| SO$_2$CH$_3$ | H | H | OCF$_3$ | H | NO$_2$ | NO$_2$ |
| Cl | H | H | OCF$_3$ | H | CF$_3$ | NO$_2$ |
| OCF$_2$CF$_2$H | H | H | Br | H | CF$_3$ | NO$_2$ |
| H | H | SO$_2$CF$_2$H | H | H | CF$_3$ | NO$_2$ |
| H | Cl | H | Cl | H | NO$_2$ | CF$_3$ |
| Br | H | SO$_2$C$_2$H$_5$ | H | H | NO$_2$ | CF$_2$ |

TABLE IV

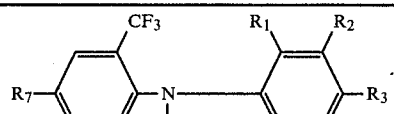

| R1 | R2 | R3 | R4 | R5 | R7 | R8 |
|---|---|---|---|---|---|---|
| Cl | H | H | SO$_2$CCl$_2$H | H | NO$_2$ | NO$_2$ |
| SO$_2$CH$_3$ | H | H | OCF$_3$ | H | NO$_2$ | NO$_2$ |
| Cl | H | H | CF$_3$ | H | NO$_2$ | CF$_3$ |
| Br | H | H | OCF$_2$CF$_2$H | H | NO$_2$ | CF$_3$ |
| OCF$_3$ | H | H | Cl | H | NO$_2$ | CF$_3$ |
| Cl | H | H | OCF$_3$ | H | CF$_3$ | NO$_2$ |
| Br | H | H | SOCF$_2$H | H | CF$_3$ | NO$_2$ |
| SOC$_2$H$_5$ | H | H | Br | H | CF$_3$ | NO$_2$ |

Formulation

Useful formulations of the compounds of Formula (I) can be prepared in conventional ways. They include dusts, solutions, suspensions, emulsions, wettable powders, emulsifiable concentrates and the like. Many of these may be applied directly. Sprayable formulations can be extended in suitable media and used at spray volumes of from a few pints to several hundred gallons per acre. High-strength compositions are primarily used as intermediates for further formulation. The formulations, broadly, contain about 1% to 99% by weight of active ingredient(s) and at least one of (a) about 0.1% to 20% surfactant(s) and (b) about 1% to 99% solid or liquid diluent(s). More specifically, they will contain these ingredients in the following approximate proportions:

|  | Percent by Weight | | |
|---|---|---|---|
|  | Active Ingredient | Diluent(s) | Surfactant(s) |
| Wettable Powders | 20–90 | 0–74 | 1–10 |
| Oil Suspensions, Emulsions, Solutions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High-Strength | 90–99 | 0–10 | 0–2 |

-continued

| Compositions | Percent by Weight | | |
|---|---|---|---|
| | Active Ingredient | Diluent(s) | Surfactant(s) |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd. Edn., Dorland Books, Caldwell, N.J. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Co., Ridgewood, New Jersey, as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, promote sticking, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084).

For further information regarding the art of formulation, see for example:

J. B. Buchanan, U.S. Pat. No. 3,576,834, Apr. 27, 1971, Col, 5, Line 36 through Col. 7, Line 70 and Ex. 1–4, 17, 106, 123–140;

R. R. Shaffer, U.S. Pat. No. 3,560,616 Feb. 2, 1971, Col. 3, Line 48 through Col. 7, Line 26 and Examples 3–9, 11–18;

E. Somers, "Formulation", Chapter 6 in Torgeson, "Fungicides", Vol, I, Academic Press, New York, 1967.

The following formulations are illustrative of those which can be prepared.

| Wettable Powder | |
|---|---|
| 1,1,1-trichloro-N-[2-chloro-5-(trifluoromethyl)phenyl]-N-[2,6-ditrifluoromethyl-4-nitrophenyl]-methane sulfenamide | 40% |
| Dioctyl sodium sulfosuccinate | 1.5% |
| Sodium ligninsulfonate | 3% |
| Low-viscosity methyl cellulose | 1.5% |
| Attapulgite | 54% |

Blend ingredients and pass through an air mill, to produce an average particle size under 15 microns, reblend, and sift through a U.S.S. No. 50 sieve (0.3 mm opening) before packaging.

All compounds of the invention may be formulated in the same manner, and dispersed in water for application.

| Wettable Powder | |
|---|---|
| 1,1,1-trichloro-N-[2-chloro-5-(trifluoromethyl)phenyl]-N-[2,6-ditrifluoromethyl-4-nitrophenyl]-methane sulfenamide | 80% |
| Sodium alkylnaphthalenesulfonate | 2% |
| Sodium ligninsulfonate | 2% |
| Synthetic amorphous silica | 3% |
| Kaolinite | 13% |

Combine ingredients in a blender, pass through a hammer mill to produce particles below 40 microns, and then reblend. Sift product through a U.S.S. No. 50 sieve (0.3 mm openings) before packaging.

| Dust | |
|---|---|
| Wettable powder (described above) | 10% |
| Pyrophyllite (powder) | 90% |

Blend the wettable powder and the pyrophyllite diluent and package. The product is suitable for use as a dust.

| Aqueous Suspension | |
|---|---|
| 1,1,1-trichloro-N-[2-chloro-5-(trifluoromethyl)phenyl]-N-[2,6-ditrifluoromethyl-4-nitrophenyl]-methane sulfenamide | 25% |
| Hydrated attapulgite | 3% |
| Crude calcium ligninsulfonate | 10% |
| Sodium dihydrogen phosphate | 0.5% |
| Water | 61.5% |

Grind the ingredients together in a sand mill until the solid particles are reduced to diameters under 10 microns. The product may be diluted with water for spray application.

| Dust Seed Coat | |
|---|---|
| 1,1,1-trichloro-N-[2-chloro-5-(trifluoromethyl)phenyl]-N-[2,6-ditrifluoromethyl-4-nitrophenyl]-methane sulfenamide | 75% |
| Permanent Red 2 B, Calcium Salt, | 5% |
| Diatomaceous Earth | 20% |

Blend the ingredients, coarsely hammermill and pass through an air mill to produce particles of active ingredient that are all below 10 microns in diameter. Reblend the product before packaging.

| Slurry Seed Coat | |
|---|---|
| 1,1,1-trichloro-N-[2-chloro-5-trifluoromethyl)phenyl]-N-[2,6-ditrifluoromethyl-4-nitrophenyl]-methane sulfenamide | 50% |
| Calcium ligninsulfonate | 4% |
| Trimethyl nonyl polyethylene glycol ether | 4% |
| Rhodamine B | 1% |
| Permanent Red 2 B, calcium salt, extended on Blanc Fixe | 1% |
| Diatomaceous earth | 40% |

Spray the liquid surfactant on the diatomaceous earth and add the other ingredients thoroughly mixed together in an efficient blender. Coarsely hammermill the mixture and pass through an air mill to produce particles of active ingredient that are less than 10 microns in diameter. Reblend the product before packaging. The product may be extended in water and applied to seed in a commercial seed treater.

Use

The compounds (I) of this invention are useful in control of mites.

Also, the compounds of this invention are useful as miticides and can be used to protect plants from damage caused by these pests. More specifically, fruits, field crops, vegetables and ornamentals can be protected.

When mites come into contact with the compounds of this invention, either in the form of direct sprays or by walking over surfaces which have been treated, they can be killed if they have been exposed to a sufficiently high dosage. While most plants are able to tolerate the presence of very small numbers of mites without apparent adverse effect, the reproductive capacity of these pests is enormous. Generally, mite populations rapidly build up, easily out-stripping parasite and predator capabilities for control. Growers noting rapid mite build-up must take immediate action to prevent damage to economically important crops. Thus, a method is needed for immediately reducing mite build-up and thereby preventing damage to important crops.

The method of this invention, namely, contact mites with a miticidally effective concentration, is a most desirable method for control of these pests. For instance, very small quantities of compounds are required for miticidal activity.

The quantity of compound needed for miticidal activity will vary depending on the specific situation. Among the variables that must be considered in deciding on the quantity of chemical to be used are the specific compound itself, the specific mite to be controlled, weather conditions, the type of crop, the stage of development of the crop, the volume of spray applied population pressure, and the interval between applications. For plant protection, solutions or suspensions containing as little as 2.5 ppm of active ingredient in a spray solution may prove effective under a given set of circumstances. For field usage, however, in high-volume applications, aqueous spray preparations containing 5-2500 ppm of active ingredient are generally considered useful. Preferred are suspensions containing 20-500 ppm, and most preferred are those containing 80-320 ppm. On an area basis, in general, 0.03 to 5.5 kilograms of active ingredient per hectare are considered acceptable, preferably 0.03 to 3 kilograms, and most preferable 0.06 to 2 kg. When applied in an orchard, spraying is continued until run-off is observed.

It may be desirable or useful to mix the compounds of this invention with other agricultural pesticides or adjuvants. Such mixtures often increase the effectiveness of the application on mites and broaden the scope of control to embrace other pests such as insects, fungi, nematodes, or bacteria. Pesticides with which the compounds of this invention may be mixed to achieve broader-spectrum activity include:

Fungicides:
methyl 2-benzimidazolecarbamate (carbendazim)
tetramethyl thiuram disulfide (thiuram)
n-dodecylguanidine acetate (dodine)
manganese ethylenebisdithiocarbamate (maneb)
1,4-dichloro-2,5-dimethoxybenzene (chloroneb)
methyl 1-(butylcarbamoyl)-2-benzimidazolecarbamate (benomyl)
N-trichloromethylthiotetrahydrophthalimide (captan)
N-trichloromethylthiophthalimide (folpet)
Bactericides:
tribasic copper sulfate
streptomycin sulfate
Acaricides:
senecioic acid, ester with 2-sec-butyl-4,6-dinitrophenol ("Morocide")
6-methyl-1,3-dithiolo[4,5-b]quinoxolin-2-one ("Morestan")
ethyl 4,4'-dichlorobenzilate (Chlorobenzilate ®)
1,1-bis(p-chlorophenyl)-2,2,2-trichloroethanol (Kelthane ®)
bis(pentachloro-2,4-cyclopentadien-1-yl) (Pentac ®)
tricyclohexyltin hydroxide (Plictran ®)
Nematicides:
S-methyl 1-(dimethylcarbamoyl)-N-(methylcarbamoyloxy)thioformimidate (Vydate ®)
S-methyl 1-carbamoyl-N-(methylcarbamoyloxy)thioformimidate
N-isopropylphosphoramidic acid, O-ethyl-O'-[4-(methylthio)-m-tolyl]diester ("Nemacur")
Insecticides:
3-hydroxy-N-methylcrotonamide(dimethylphosphate)ester (Azodrin ®)
methylcarbamic acid, ester with 2,3-dihydro-2,2-dimethyl-7-benzofuranol (Furadan ®)
O-[2,4,5-trichloro-α-(chloromethyl)benzyl]phosphoric acid, O',O'-dimethyl ester (Gardona ®)
2-mercaptosuccinic acid, diethyl ester, S-ester with thionophosphoric acid, dimethyl ester (Malathion ®)
phosphorothioic acid, O,O-dimethyl,O-p-nitrophenyl ester (methyl parathion)
methylcarbamic acid, ester with α-naphthol (Sevin ®)
methyl O-(methylcarbamoyl)thiolacetohydroxamate (methomyl)
O,O-diethyl-O-(2-isopropyl-4-methyl-6-pyrimidylphosphorothioate (Diazinon ®)
octachlorocamphene (toxaphene)
O-ethyl O-p-nitrophenyl phenylphosphonothioate (EPN)
cyano(3-phenoxyphenyl)methyl 4-chloro-α-(1-methylethyl)benzeneacetate (Pydrin ®)
(3-phenoxyphenyl)methyl(+)-cis,trans-3-(2,2-dichloroethenyl)-2,2-dimethylcyclopropanecarboxylate (Ambush ®)
O-ethyl-S-(p-chlorophenyl)ethylphosphonodithioate (Curacron ®)
phosphorothiolothionic acid, O-ethyl-O-[4-(methylthio)phenyl]-S-n-propyl ester (Bolstar ®)

The agricultural chemicals listed above are merely exemplary of compounds that may be mixed with the active compounds of this invention.

The compounds are considered especially suited for the protection of living plants such as fruit-bearing trees, nut-bearing trees, ornamental trees, forest trees, vegetable crops, horticultural crops (including ornamentals, small fruit and berries) and grain and seed crops. Apple trees, peach trees, cotton, citrus trees, beans and peanuts are particularly susceptible to mite damage and can be protected by application of the compounds of this invention. To assure control throughout the growing season (e.g., June through August in the Northern Hemisphere) multiple applications at desired intervals can be utilized.

Many species of mites can be controlled by the compounds of this invention. The following is a list of representative susceptible mites along with the types of damage that they can cause: *Panonychus ulmi* (European red mite) and *Tetranychus urticae* (two-spotted mite) which are commonly called "orchard mites," and which attack a great many deciduous trees, such as apple, pear, cherry, plum and peach trees; *Tetranychus atlanticus* (Atlantic or strawberry mite), *T. cinnabarinus* (carmine spider mite) and *T. pacificus* (Pacific mite); which attack cotton and numerous other crop plants; *Paratetranychus citri* (citrus red mite) and others which attack citrus; *Phyllocoptruta oleivora* which causes citrus rust; *Bryobia praetiosa* (clover mite) which attacks clover, alfalfa and other crops; and *Aceria neocynodomis* which attacks grasses and other plants.

The compounds of this invention are also useful as plant disease control agents. They are considered effective for the control of a broad spectrum of plant diseases as represented by but not limited to soil borne fungal pathogens *Rhizoctonia solani* and *Phytophthora parasitica*, a pathogen that infects seeds and seedlings, *Helminthosporium oryzae*, a fungus that attacks stems and leaves, *Puccinia graminis*, a fungus that causes leaf and fruit lesions, *Venturia inaequalis*, and a fruit and vegetable rotting fungus, *Sclerotinia sclerotiorum*. Diseases of a wide variety of ornamental, vegetable cereal and fruit crops can be controlled by the compounds of this invention.

Disease control is accomplished by applying the compound to the portion of the plant to be protected such as the roots, stems, foliage, fruit, seeds, tubers or bulbs, or to the media (soil) in which the plants to be protected are growing.

Rates of application for these compounds will be influenced by many factors of the environment and must be determined under use conditions. Seed and seedlings can normally be protected when seed is treated at a rate of from 0.06 to about 3 grams per kilogram of seed. Plants growing in soil treated at a concentration of from 0.1 to about 20 kg/ha can be protected from disease. Compositions of this invention may contain, in addition to a compound of this invention, conventional pesticides, such as insecticides, miticides, bactericides, nematicides, fungicides or other agricultural chemicals such as growth modifying agents. Representative examples of these are listed above.

The compounds of this invention are also useful as insect ovicides. The species that may be controlled include but are not limited to beet armyworm (*Spodoptera exigua*), and southern armyworm (*Spodoptera frugiperda*), potato tuberworm (*Phthorimaea operculella*), cottom bollworm (*Heliothis zea*) and tobacco budworm (*Heliothis virescens*).

Spray applications of 0.1–2 kg per hectare to foliage containing eggs will prevent further development of the embroyos thereby protecting the plant from the feeding effect of voracious larvae. Plants to be protected include a wide range of vegetable and field crops, ornamentals and forest trees.

What is claimed is:

1. A compound of the formula

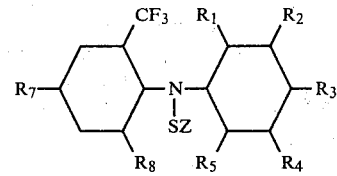

wherein
$R_1$, $R_3$ and $R_4$ independently are H, F, Cl, Br, $NO_2$, $CF_3$, $OCF_3$, $OCF_2CF_2H$ or $S(O)_kR_6$;
$R_2$ is H, F, Cl, Br, $NO_2$ or $CF_3$;
$R_5$ is H or F;
$k$ is 0, 1, or 2;
$R_6$ is $C_1$–$C_2$ alkyl or $C_1$–$C_2$ alkyl substituted with 2 to 4 atoms of Cl, F or combinations thereof;
$R_7$ is $NO_2$ or $CF_3$;
$R_8$ is $NO_2$ or $CF_3$;
Z is $CCl_3$, $CCl_2F$, $CCl_2CCl_2H$ or $CCl_2CFCL_2$;
provided that when $R_1$ is $NO_2$ or $CF_3$, then $R_3$ must be H or F;
provided that at least two of the substituents $R_1$, $R_2$, $R_3$, and $R_4$ are H, F or combinations thereof;
provided that when two of the substituents $R_1$, $R_2$, $R_3$ and $R_4$ are $NO_2$, $S(O)_kR_6$ or combinations thereof, they are not ortho to each other;
provided that $R_7$ and $R_8$ cannot both be $NO_2$ unless one of $R_1$, $R_3$, or $R_4$ is $S(O)_kR_6$; and
provided that $R_7$ and $R_8$ cannot both be $CF_3$.

2. A compound of claim 1 where
$R_2$ is H, F, Cl or Br;
$R_3$ is H, F, Cl, Br or $S(O)_kR_6$; and
$R_4$ is F, Cl, Br, $CF_3$, $OCF_3$, $OCF_2CF_2H$ or $S(O)_kR_6$.

3. A compound of claim 1 where
Z is $CCl_3$;
$R_1$ and $R_4$ independently are Cl, $CF_3$, $OCF_3$, $OCF_2CF_2H$ or $S(O)_kR_6$;
$R_2$, $R_3$ and $R_5$ are H.

4. The compound of claim 1 which is 1,1,1-trichloro-N-[2-chloro-5-(trifluoromethyl)phenyl]-N-[2,6-ditrifluoromethyl-4-nitrophenyl]methane sulfenamide.

5. An agricultural composition for control of mites, fungus disease of a plant or insects comprising a diluent, surfactant or mixtures thereof and a miticidally, fungicidally, or insecticidally effective amount of a compound of claim 1.

6. An agricultural composition for control of mites, fungus disease of a plant or insects comprising a diluent, surfactant or mixtures thereof and a miticidally, fungicidally, or insecticidally effective amount of a compound of claim 2.

7. An agricultural composition for control of mites, fungus disease of a plant or insects comprising a diluent, surfactant or mixtures thereof and a miticidally, fungicidally, or insecticidally effective amount of a compound of claim 3.

8. An agricultural composition for control of mites, fungus disease of a plant or insects comprising a diluent, surfactant or mixtures thereof and a miticidally, fungicidally, or insecticidally effective amount of the compound of claim 4.

9. A method for control of mites, fungus disease of a plant or insect eggs which comprises applying to a locus to be protected a miticidally, fungicidally or ovicidally effective amount of a compound of claim 1.

10. A method for control of mites, fungus disease of a plant or insect eggs which comprises applying to a locus to be protected a miticidally, fungicidally or ovicidally effective amount of a compound of claim 2.

11. A method for control of mites, fungus disease of a plant or insect eggs which comprises applying to a locus to be protected a miticidally, fungicidally or ovicidally effective amount of a compound of claim 3.

12. A method for control of mites, fungus disease of a plant or insect eggs which comprises applying to a locus to be protected a miticidally, fungicidally or ovicidally effective amount of the compound of claim 4.

* * * * *